US011911002B2

United States Patent
Hashi et al.

(10) Patent No.: US 11,911,002 B2
(45) Date of Patent: Feb. 27, 2024

(54) OVERTUBE DEVICE

(71) Applicant: OLYMPUS CORPORATION, Tokyo (JP)

(72) Inventors: Hiroshi Hashi, Tokyo (JP); Masaru Yanagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1020 days.

(21) Appl. No.: 16/717,148

(22) Filed: Dec. 17, 2019

(65) Prior Publication Data

US 2020/0121361 A1    Apr. 23, 2020

Related U.S. Application Data

(63) Continuation of application No. PCT/JP2017/023082, filed on Jun. 22, 2017.

(51) Int. Cl.
*A61B 1/00* (2006.01)
*A61M 25/01* (2006.01)
(Continued)

(52) U.S. Cl.
CPC ...... *A61B 1/00154* (2013.01); *A61B 1/00135* (2013.01); *A61M 25/0113* (2013.01);
(Continued)

(58) Field of Classification Search
CPC ... A61B 1/00135; A61B 1/00154; A61B 1/31; A61B 90/50; A61B 2017/00017;
(Continued)

(56) References Cited

U.S. PATENT DOCUMENTS

2003/0233025 A1    12/2003    Saadat et al.
2003/0233026 A1    12/2003    Saadat et al.
(Continued)

FOREIGN PATENT DOCUMENTS

JP    2001-017386 A    1/2001
JP    2006-505302 A    2/2006
(Continued)

OTHER PUBLICATIONS

International Search Report dated Aug. 8, 2017 received in PCT/JP2017/023082.

*Primary Examiner* — Jocelin C Tanner
(74) *Attorney, Agent, or Firm* — Scully, Scott, Murphy & Presser, P.C.

(57) ABSTRACT

An overtube device includes: a tube body having a bending part and a main body part; a wire having a distal end part fixed to the bending part and a proximal end part positioned on the proximal end side and extending along a longitudinal axis; an operation part capable of pulling the wire to the proximal end side; and an overtube base configured to fix the tube body in a longitudinal axis direction so as not to advance and retract, and configured so that the operation part is provided in a state where the wire is pulled toward the proximal end side of the wire until a curved shape of the bending part is held. In a state where the operation part is mounted on the overtube base, the overtube base holds the wire in a state where the wire is pulled toward the proximal end side of the wire.

17 Claims, 12 Drawing Sheets

(51) Int. Cl.
 *A61M 25/06* (2006.01)
 *A61B 1/31* (2006.01)
 *A61B 17/00* (2006.01)
 *A61B 17/34* (2006.01)

(52) U.S. Cl.
 CPC .......... *A61M 25/0662* (2013.01); *A61B 1/31* (2013.01); *A61B 2017/00115* (2013.01); *A61B 2017/00314* (2013.01); *A61B 2017/00327* (2013.01); *A61B 2017/00367* (2013.01); *A61B 2017/3452* (2013.01)

(58) Field of Classification Search
 CPC .......... A61B 2017/00115; A61B 2017/00314; A61B 2017/00327; A61B 2017/0034; A61B 2017/00367; A61B 2017/3452; A61B 2090/034; A61B 2090/0808; A61M 25/0113; A61M 25/0136; A61M 25/0147; A61M 25/0662
 See application file for complete search history.

(56) References Cited

U.S. PATENT DOCUMENTS

| | | | |
|---|---|---|---|
| 2003/0233027 A1 | 12/2003 | Ewers et al. | |
| 2003/0233056 A1 | 12/2003 | Saadat et al. | |
| 2003/0233057 A1 | 12/2003 | Sadaat et al. | |
| 2003/0233058 A1 | 12/2003 | Ewers et al. | |
| 2003/0233066 A1* | 12/2003 | Ewers | A61B 1/00082 604/27 |
| 2004/0162568 A1 | 8/2004 | Saadat et al. | |
| 2004/0225183 A1 | 11/2004 | Michlitsch et al. | |
| 2004/0225305 A1 | 11/2004 | Ewers et al. | |
| 2005/0075653 A1 | 4/2005 | Saadat et al. | |
| 2005/0137454 A1 | 6/2005 | Saadat et al. | |
| 2005/0137455 A1 | 6/2005 | Ewers et al. | |
| 2005/0137456 A1 | 6/2005 | Saadat et al. | |
| 2005/0245945 A1 | 11/2005 | Ewers et al. | |
| 2006/0058582 A1 | 3/2006 | Maahs et al. | |
| 2006/0111614 A1 | 5/2006 | Sadaat et al. | |
| 2008/0188868 A1 | 8/2008 | Weitzner et al. | |
| 2008/0188869 A1 | 8/2008 | Weitzner et al. | |
| 2008/0188871 A1 | 8/2008 | Smith et al. | |
| 2008/0188890 A1 | 8/2008 | Weitzner et al. | |
| 2008/0221391 A1 | 9/2008 | Weitzner et al. | |
| 2008/0243176 A1 | 10/2008 | Weitzner et al. | |
| 2008/0262301 A1* | 10/2008 | Gibbons | A61B 1/01 600/114 |
| 2009/0062606 A1 | 3/2009 | Ueda et al. | |
| 2010/0211086 A1 | 8/2010 | Ewers et al. | |
| 2011/0046442 A1 | 2/2011 | Matsushita et al. | |
| 2012/0004502 A1 | 1/2012 | Weitzner et al. | |
| 2014/0188054 A1 | 7/2014 | Iijima et al. | |
| 2014/0343433 A1* | 11/2014 | Elbert | A61B 8/54 600/467 |
| 2015/0238180 A1 | 8/2015 | Weitzner et al. | |
| 2016/0089007 A1 | 3/2016 | Weitzner et al. | |
| 2017/0325904 A1* | 11/2017 | Hyodo | B25J 18/06 |

FOREIGN PATENT DOCUMENTS

| | | | |
|---|---|---|---|
| JP | 2009-056054 A | 3/2009 | |
| JP | 2009-279412 A | 12/2009 | |
| JP | 2010-207340 A | 9/2010 | |
| JP | 2011-036601 A | 2/2011 | |
| JP | 2014-124475 A | 7/2014 | |
| JP | 2016-039918 A | 3/2016 | |
| WO | 92/019147 A1 | 11/1992 | |
| WO | 03/105563 A2 | 12/2003 | |
| WO | WO-2015125914 A1 * | 8/2015 | .............. A61B 1/00 |

* cited by examiner

OVERTUBE DEVICE

CROSS REFERENCE TO RELATED APPLICATIONS

This application is a continuation application based on a PCT Patent Application No. PCT/JP2017/023082, filed on Jun. 22, 2017, the content of which is incorporated herein by reference.

BACKGROUND

Technical Field

The present invention relates to an overtube device.

Background Art

Conventionally, an overtube for assisting a procedure for inserting a medical device such as an endoscope or a treatment tool into a body cavity or a lumen, for example, a deep part of a large intestine or a small intestine is known. The overtube is flexible and has a lumen (channel, conduit) through which a medical device such as an endoscope or a treatment instrument can be inserted.

The insertion part of the medical device is inserted through the lumen of the overtube, and is inserted into the body cavity or the lumen together with the overtube. Further, when the overtube is inserted into the body cavity or lumen first, the insertion part of the medical device is inserted along the lumen of the overtube.

Thus, the overtube functions as a guide for the insertion part of the medical device. As a result, even when the body cavity or lumen has a bending part, the insertion part of the medical device can be smoothly inserted into the body cavity or deep part of the lumen.

Japanese Unexamined Patent Application, First Publication No. 2009-279412 (hereinafter referred to as Patent Document 1) discloses an overtube with a shape lock function. A part of the overtube described in Patent Document 1 includes a plurality of telescopic elements. By pulling the wires inserted through the plurality of telescopic elements toward the proximal end in the longitudinal axis direction of the overtube, the intimate force between the telescopic elements is increased. As a result, the shape of the overtube is temporarily fixed by the frictional force generated between the telescopic elements.

By the overtube whose shape of the overtube is temporarily fixed, medical devices such as an endoscope and a treatment instrument can be arranged stably when treating an affected part in a flexible body cavity or lumen. Moreover, by the overtube whose shape is temporarily fixed, it is possible to more reliably guide the distal end of the treatment instrument to the distal end of the overtube.

SUMMARY

An overtube device includes: a tube body having a bending part that is curvable on a distal end side, and a main body part that is continuous with the bending part and extends to a proximal end side; a wire having a distal end part fixed to the bending part, and a proximal end part positioned on the proximal end side of the main body part and extending along a longitudinal axis of the main body part; an operation part that is mounted on the proximal end side of the main body, is attached to the proximal end part of the wire, and is configured to be capable of pulling the wire to the proximal end side of the wire; and an overtube base configured to fix the tube body in a longitudinal axis direction so as not to advance and retract, and configured so that the operation part is provided in a state where the wire is pulled toward the proximal end side of the wire until a curved shape of the bending part is held. In a state where the operation part is mounted on the overtube base, the overtube base holds the wire in a state where the wire is pulled toward the proximal end side of the wire.

By separating the operation part, which is mounted on the overtube base, from the overtube base, the tube body may advance and retract in the longitudinal axis direction, the operation part may not pull the wire to the proximal end side of the wire, and a holding of the curved shape of the bending part may be released.

The operation part may include: an operation part main body; and a wire operation part that is held so as to be relatively movable with respect to the operation part main body and to which the proximal end part of the wire is attached. By moving the wire operation part relative to the operation part main body, the wire may be pulled toward the proximal end side of the wire.

The operation part main body may include an advance/retreat stopper engaging part. The wire operation part may include a wire operation lever engaging part. The overtube base may include an advance/retreat stopper engaged with the advance/retreat stopper engaging part, and a wire operation lever engaged with the wire operation part while keeping a relative position of the advance/retreat stopper constant. The operation part may be mounted on the overtube base, so that the advance/retreat stopper may be engaged with the advance/retreat stopper engaging part, and simultaneously the wire operation lever may be engaged with the wire operation lever engaging part.

The wire operation lever may be configured to be movable to either a first position or a second position. When the wire operating lever that engages with the wire operating lever engaging part is provided at the first position, the operation part may not pull the wire toward the proximal end of the wire, and a holding of the curved shape may be released. When the wire operating lever that engages with the wire operating lever engaging part is provided at the second position, the operation part may pull the wire toward the proximal end of the wire, and the curved shape may be held.

The overtube base may include a wire operation lever drive part that moves the wire operation lever to either the first position or the second position.

The wire operation lever drive part may have a button, and by operating the button, the wire operation lever may be moved from the first position to the second position.

The overtube base may further include an engagement sensor, to detect that the operation part is mounted on the overtube base.

The overtube base may further include an engagement display part. When the engagement sensor detects a mounting of the operation part on the overtube base, the engagement display part may display indicating of the mounting.

The wire may be a plurality of wires. The overtube base may be configured such that the operation part is provided in a state where the plurality of wires are pulled simultaneously on a proximal end side of the plurality of wires.

DETAILED DESCRIPTION OF THE PREFERRED EMBODIMENTS

First Embodiment

A first embodiment of the present invention will be described with reference to FIGS. 1 to 18. In addition, in order to make the drawings easy to see, the thicknesses and dimensional ratios of the respective constituent elements are appropriately adjusted.

Figure 1:
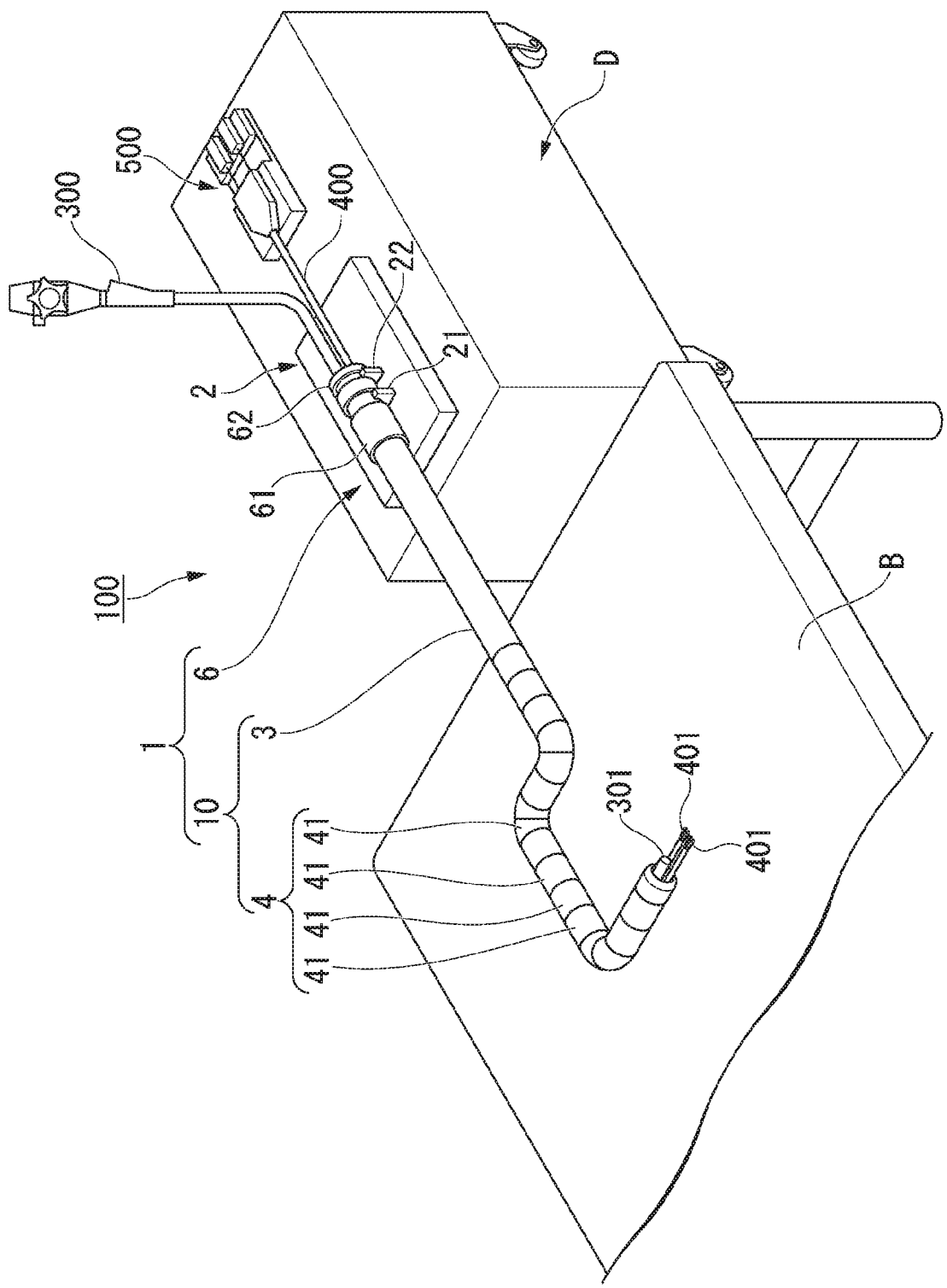
FIG. 1 is a diagram showing an overall configuration of an overtube device according to a first embodiment of the present invention.

FIG. 1 is a diagram showing an overall configuration of an overtube device 100 according to the present embodiment.

The overtube device 100 includes an overtube 1 and an overtube base 2.

Figure 2:
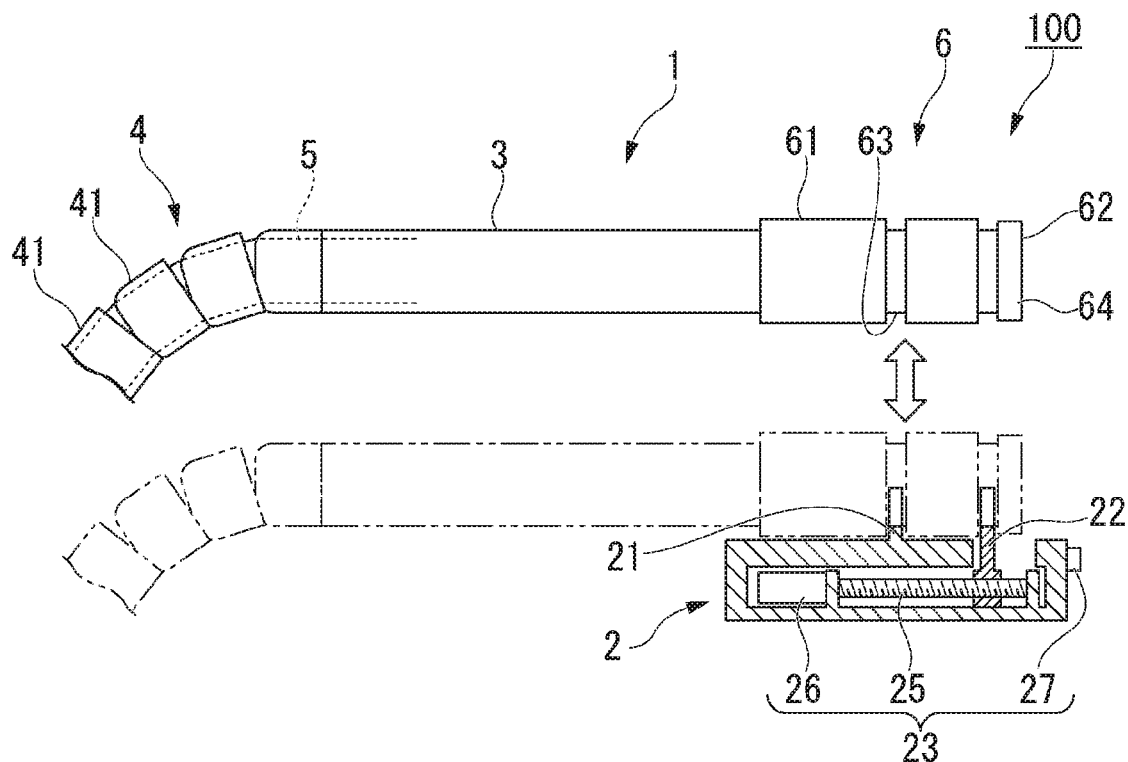
FIG. 2 is a side view of the overtube device.
Figure 3:
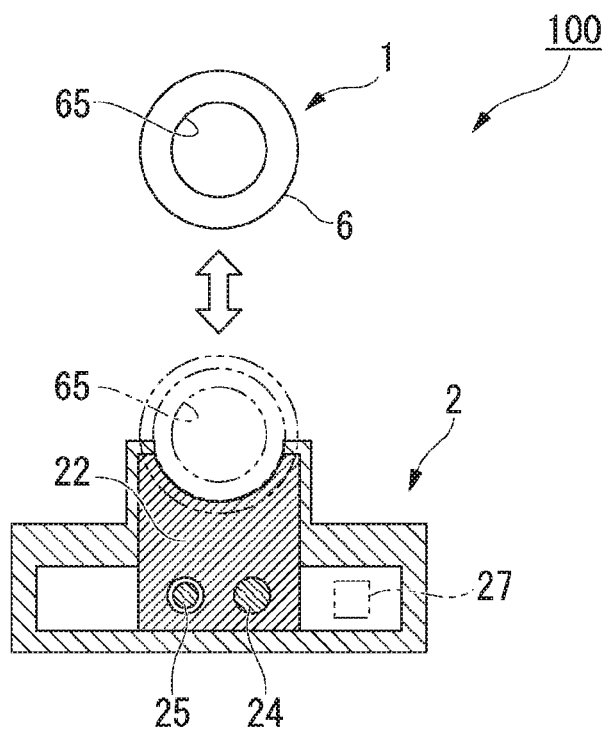
FIG. 3 is a side view of the overtube device as seen from the longitudinal axis direction.

FIG. 2 is a side view of the overtube device 100. FIG. 3 is a side view of the overtube device 100 as viewed from the proximal end side in the longitudinal axis direction. As shown in FIGS. 2 and 3, the overtube 1 is detachably attached to the overtube base 2.

As shown in FIGS. 1 and 2, the overtube 1 includes a tube body 10, a wire 5, and the operation part 6 provided at the proximal end of a flexible tube part 3. The tube body 10 has a bending part 4 that can be bent on the distal end side, and has the flexible tube part (main body part) 3 that extends to the proximal end side in connection with the bending part 4.

Figure 4:
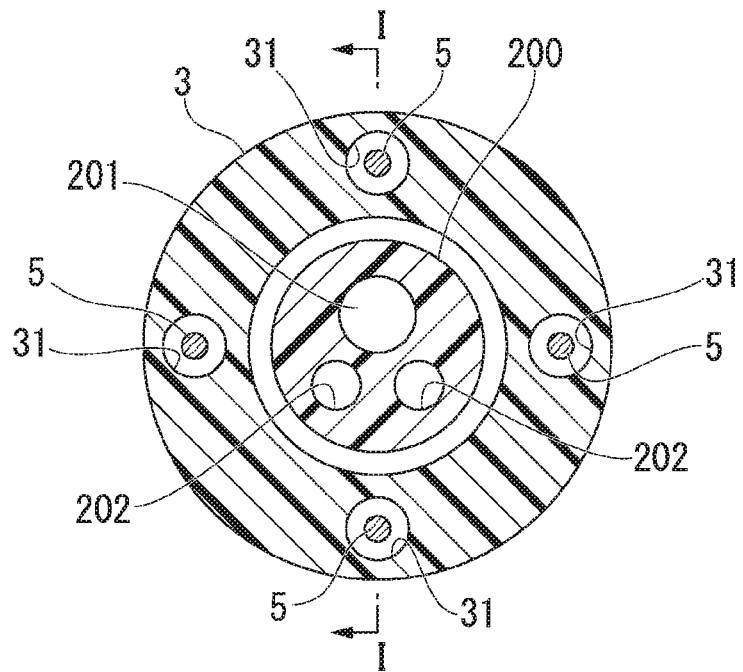
FIG. 4 is a cross-sectional view of a flexible tube part of the overtube device.

FIG. 4 is a cross-sectional view of the flexible tube part 3.

The flexible tube part 3 is a tubular member formed of a flexible material such as silicone, for example, and a multi-lumen tube 200 described later is inserted through the inside thereof as shown in FIG. 4.

As shown in FIG. 4, the flexible tube part 3 is provided with four wire lumens 31 through which the wire 5 for temporarily fixing (shape locking) the shape of the bending part 4 described later is inserted. As shown in FIG. 4, the four wire lumens 31 are arranged at positions that equally divide the circumference around the longitudinal axis of the flexible tube part 3.

As shown in FIGS. 1 and 2, the bending part 4 is configured by arranging a plurality of bending pieces 41 arranged in the axial direction, and is provided at the distal end of the flexible tube part 3. In the overtube 1 of FIG. 2, only the four bending pieces 41 on the proximal end side among the plurality of bending pieces 41 are shown for the sake of simplicity.

The bending piece 41 is a short cylindrical member, and the internal space is open at both ends. The plurality of bending pieces 41 are overlapped so that the internal space of the adjacent bending pieces 41 is a continuous space. A multi-lumen tube 200 described later is inserted through the continuous internal space.

Figure 5:
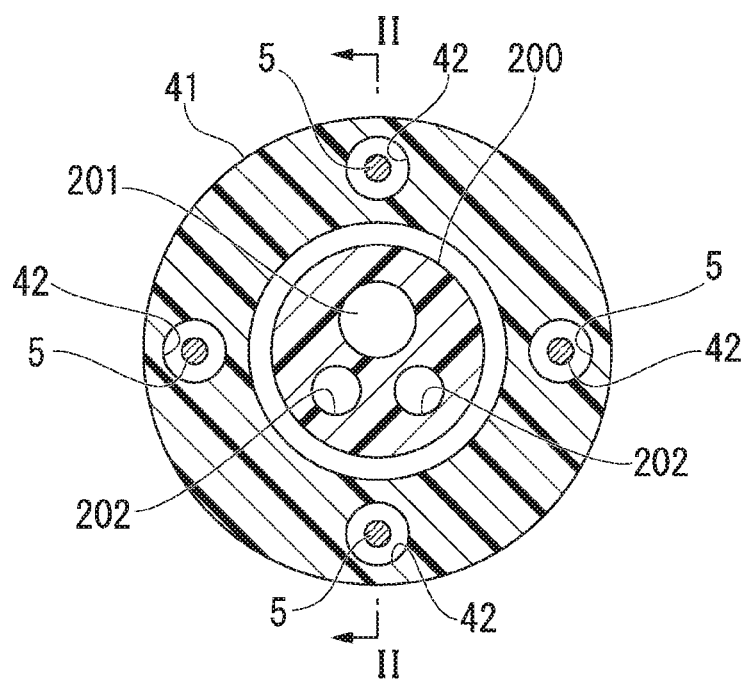
FIG. 5 is a cross-sectional view of a bending piece of the overtube device.

FIG. 5 is a cross-sectional view of the bending piece 41.

As shown in FIG. 5, all the bending pieces 41 are provided with four wire lumens 42 in the same manner as the wire lumen 31 provided in the flexible tube part 3. As shown in FIG. 5, the four wire lumens 42 are arranged at positions that equally divide the circumference around the longitudinal axis of the bending part 4.

The wire 5 has a distal end part fixed to the bending part 4 and a proximal end part located on the proximal end side of the flexible tube part 3, and extends along the longitudinal axis of the flexible tube part 3. The wire 5 is inserted through all the bending pieces 41 and the wire lumens (31, 42) of the flexible tube part 3. The distal end of the wire 5 is attached to the bending piece 41 on the most distal side. The number of wires 5 is preferably equal to or more than two.

Since the wires 5 are inserted through all the bending pieces 41, the bending pieces 41 are not separated from each other. By moving the bending piece 41 relative to the adjacent bending piece 41, the entire bending part 4 can be bent. However, when the wire 5 inserted through the inside of the bending part 4 is not loose, the bending part 4 cannot be further bent from the current curved shape.

The wire 5 is pulled toward the proximal end side of the wire 5, the bending pieces 41 are in close contact with each other, and a frictional resistance occurs between the bending pieces 41, thereby the curved shape of the bending part 4 is held (fixed). In a case where at least two wires 5 are provided, when a plurality of wires 5 are simultaneously pulled toward the proximal end side of the wires 5, the bending pieces 41 come into close contact with each other, and friction resistance occurs between the bending pieces 41, thereby the curved shape of the bending part 4 is held (fixed). In the following description, holding (fixing) the curved shape of the bending part 4 by the overtube base 2 to be described later in a state where the wire 5 (the plurality of wires 5) is pulled to the proximal end side of the wire 5 until the curved shape of the bending part 4 is held (fixed) is referred to as "activating the shape lock function" of the bending part 4. Moreover, releasing the hold (fixing) of the curved shape of the bending part 4 by releasing the pulling of the wire 5 by the overtube base 2 to be described later is referred to as "disabling the shape lock function". The means for pulling the wire 5 to the proximal end side of the wire 5 may be electric pulling or manual pulling.

As shown in FIG. 2, the bending piece 41 on the distal end side in the longitudinal axis direction of the bending part 4 is dome shaped. By the bending part 4 configured by such bending pieces 41, the contact part between adjacent bending pieces 41 can be increased as much as possible when the bending piece 41 is relatively moved so that the entire bending part 4 is bent. By increasing the contact part between the adjacent bending pieces 41, the frictional resistance acting between the bending pieces 41 can be increased, and the bending part 4 can more suitably perform the shape lock function.

Figure 6:
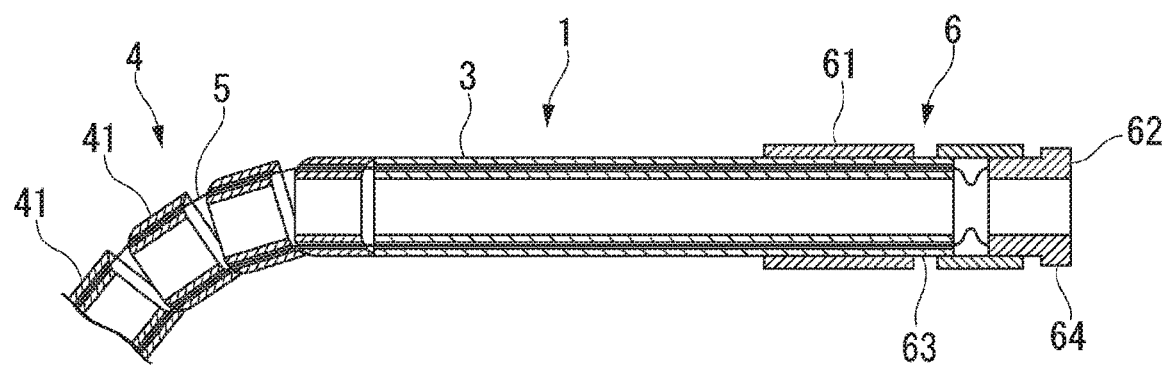
FIG. 6 is a cross-sectional view of the overtube in which the shape lock function of the overtube device is invalidated.
Figure 7:
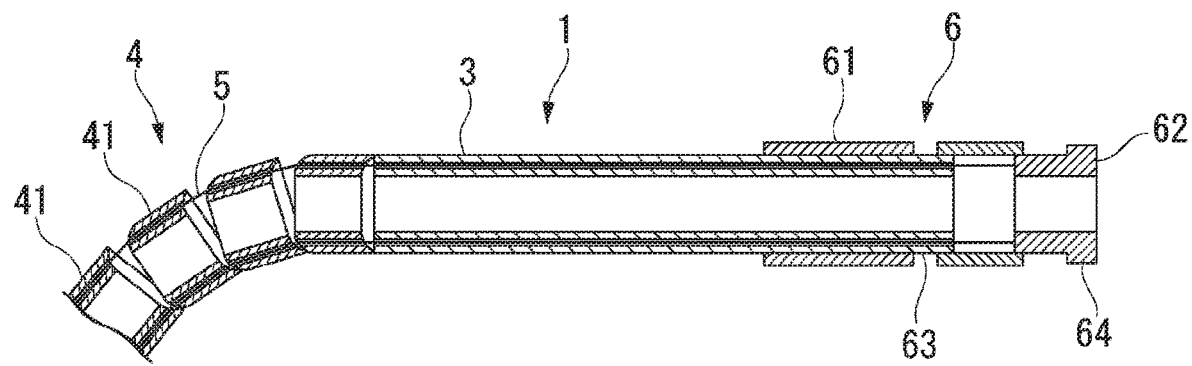
FIG. 7 is a cross-sectional view of the overtube in which the shape lock function of the overtube device is activated.

FIGS. 6 and 7 are diagrams for explaining the drive mechanism of the shape lock function of the overtube 1, and are sectional views taken along the line I-I in FIG. 4 and the line II-II in FIG. 5. Note that the description of the multi-lumen tube 200 is omitted.

FIG. 6 is a cross-sectional view of the overtube 1 in which the shape lock function is invalidated. On the other hand, FIG. 7 is a cross-sectional view of the overtube 1 in which the shape lock function is activated.

As shown in FIG. 6, in the overtube 1 in which the shape lock function is invalidated, the wire 5 is loose. Therefore, the bending part 4 can be bent until the wire 5 is not loosened.

On the other hand, as shown in FIG. 7, the wire 5 is not loose in the overtube 1 in which the shape lock function is activated. Therefore, it is limited to further bend the bending part 4 from the current curved shape. That is, when the operation part 6 is mounted (attached) to the overtube described later in a state where the wires 5 (the plurality of wires 5) are pulled simultaneously to the proximal end side of the wires 5 until the curved shape of the bending part 4 is held, the wire 5 is held in a state of being pulled toward the proximal end side. As a result, the curved shape of the bending part 4 is held.

As shown in FIGS. 6 and 7, the operation part 6 includes an operation part main body 61 to which the proximal end side of the flexible tube part 3 is connected, and a wire operation part 62 provided slidably with respect to the operation part main body 61.

The operation part main body 61 is a tubular member made of a material having high rigidity. As shown in FIG. 2, its outer diameter is larger than the outer diameter of the flexible tube part 3, and it is formed in a shape that is easy for an operator to grasp.

As shown in FIG. 2, a concave advance/retract stopper engaging part 63 that engages with an advance/retract stopper 21 of the overtube base 2 described later is formed on the outer periphery of the operation part main body 61.

As shown in FIGS. 6 and 7, the internal space of the operation part main body 61 communicates with the internal space of the flexible tube part 3.

As shown in FIGS. 6 and 7, the wire operation part 62 is a tubular member having an outer diameter smaller than the inner diameter of the operation part main body 61, and is held so as to be relatively movable in the longitudinal axis direction with respect to the operation part main body 61. Further, the proximal end part of the wire 5 is attached to the wire operation part 62. When the operator moves the wire operation part 62 relative to the operation part main body 61 toward the proximal end side, the wire operation part 62 pulls the wire 5 to increase the tension of the wire 5. By increasing the frictional force of the portion where the bending pieces 41 contact with each other and holding the curved shape, the shape lock function of the bending part 4 can be activated.

On the proximal end side of the wire operation part 62, a wire operation lever engaging part 64 that engages with a wire operation lever 22 of the overtube base 2 described later is formed. As shown in FIGS. 6 and 7, the wire operation lever engaging part 64 is a convex portion having an outer diameter larger than the outer diameter of the other portion of the wire operation part 62.

As shown in FIG. 3, the proximal end of the wire operation part 62 is open, and the multi-lumen tube 200 is inserted through the opening 65. The inserted multi-lumen tube 200 passes through the internal space of the operation part main body 61, the flexible tube part 3, and the bending part 4, and protrudes from the distal end of the bending part 4.

The overtube base 2 is a base on which the operation part 6 can be detachably attached. In the present embodiment, the overtube base 2 is fixed on a carriage D with casters, as shown in FIG. 1. When using the overtube device 100, the casters of the carriage D are fixed so as not to move. That is, the overtube base 2 is fixed so that the relative position of the overtube base 2 relative to the bed B, where a patient into which the overtube 1 is inserted lies, does not change during the treatment.

As shown in FIGS. 2 and 3, the overtube base 2 includes an advance/retreat stopper 21, a wire operation lever 22, and a wire operation lever drive part 23.

The advance/retreat stopper 21 is a convex member formed on the overtube base 2, and engages with the advance/retreat stopper engaging part 63 of the operation part main body 61. Thereby, the operation part main body 61 and the overtube 1 cannot advance or retreat in the longitudinal axis direction.

Since the relative position of the overtube base 2 with the bed B where the patient under treatment lies is fixed, the overtube 1, which is fixed so as not to advance or retract in the longitudinal axis direction by the advance/retreat stopper 21 formed on the overtube base 2, is also fixed so as not to advance or retract in the longitudinal axis direction with respect to the bed B where the patient under treatment lies.

By releasing the engagement between the advance/retreat stopper 21 and the advance/retreat stopper engaging part 63 of the operation part main body 61, the operation part main body 61 and the overtube 1 can advance and retreat in the longitudinal axis direction.

The wire operation lever 22 is a convex member formed on the overtube base 2 and engages with the wire operation lever engaging part 64 of the wire operation part 62.

The wire operation lever 22 is configured to be movable to either the first position or the second position by the wire operation lever drive part 23.

Figure 8:
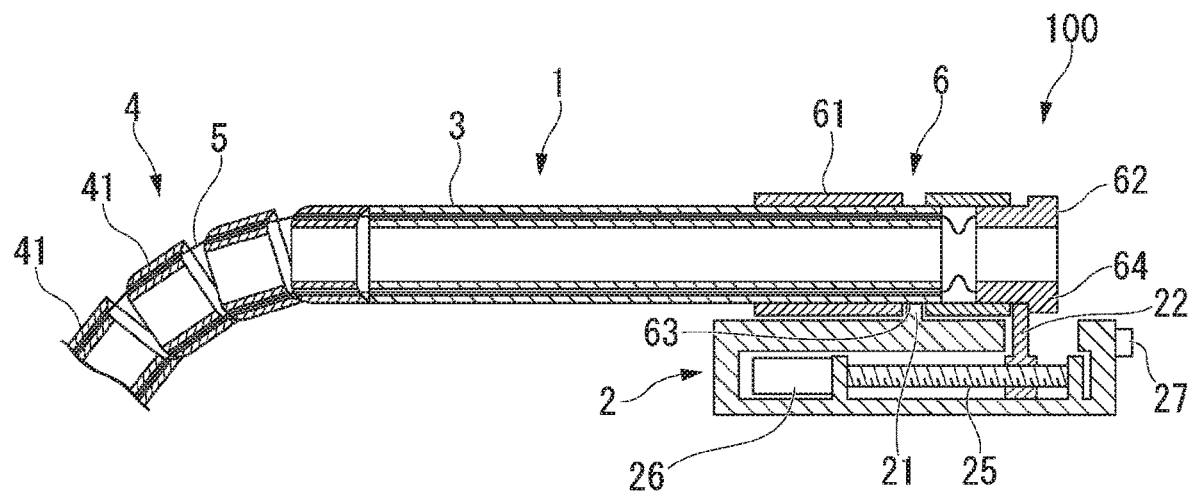
FIG. 8 is a cross-sectional view when the wire operation lever of the overtube device is provided at a first position.

FIG. 8 is a cross-sectional view of the overtube device 100 when the wire operation lever 22 is provided at the first position. On the other hand, FIG. 9 is a cross-sectional view of the overtube device 100 when the wire operation lever 22 is provided at the second position.

The second position as viewed from the first position is located in the longitudinal axis direction of the overtube 1 when the overtube 1 is mounted (attached) on the overtube base 2.

Figure 9:
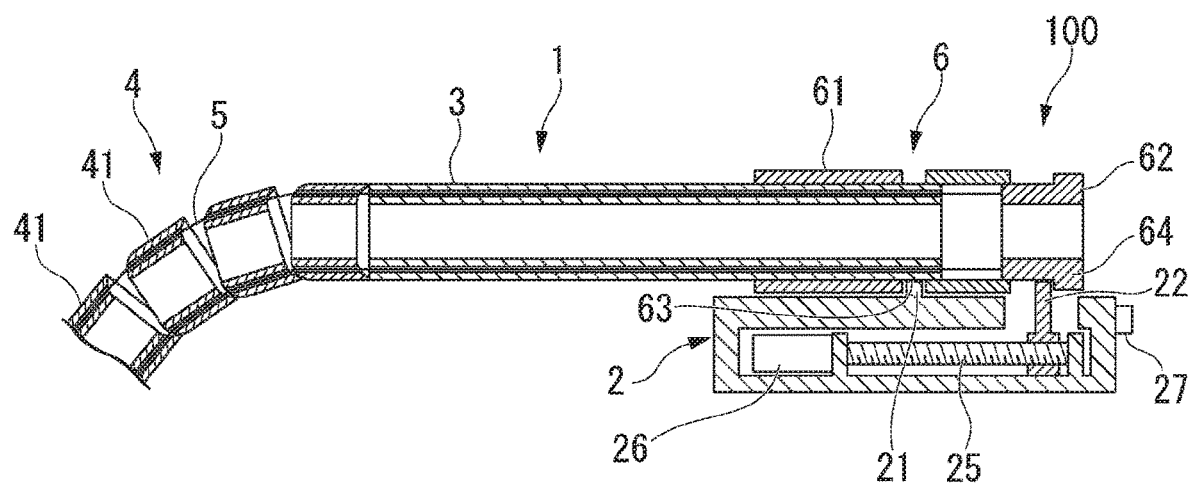
FIG. 9 is a cross-sectional view when the wire operation lever of the overtube device is provided at a second position.

The wire operation lever 22 arranged at the second position shown in FIG. 9 has a longer relative distance from the advance/retreat stopper 21 than the wire operation lever 22 arranged at the first position shown in FIG. 8. Therefore, the relative distance between the wire operation part 62 engaged with the wire operation lever 22 provided at the second position and the operation part main body 61 engaged with the advance/retreat stopper 21 is longer than the relative distance between the wire operation part 62 engaged with the wire operation lever 22 provided at the first position and the operation part main body 61 engaged with the advance/retreat stopper 21.

When the wire operation lever 22 is provided at the first position, as shown in FIG. 2, the advance/retreat stopper 21 is engaged with the advance/retreat stopper engaging part 63, and the wire operation lever 22 is engaged with the wire operation lever engaging part 64, thereby the overtube 1 is mounted (attached) on the overtube base 2.

The first position and the second position of the wire operation lever 22 are adjusted so as to fix the wire operation part 62 as follows.

As shown in FIG. 8, when the wire operating lever 22 that engages with the wire operating lever engaging part 64 is provided at the first position, the wire operation part 62 does not pull the wire 5, and the shape lock function of the bending part 4 is invalidated.

As shown in FIG. 9, when the wire operating lever 22 that engages with the wire operating lever engaging part 64 is provided at the second position, the wire operation part 62 pulls the wire 5 and holds the state in which the wire 5 (the plurality of wires 5) is pulled, and the shape lock function of the bending part 4 is activated. That is, the overtube base 2 can hold the wire 5 in a state where the wires 5 (the plurality of wires 5) are simultaneously pulled toward the proximal end side until the curved shape of the bending part 4 is held.

By releasing the engagement between the wire operation lever 22 and the wire operation lever engaging part 64, the wire operation lever engaging part 64 and the wire operation part 62 can be moved relative to the operation part main body 61.

The wire operation lever drive part 23 moves the wire operation lever from the first position to the second position, or from the second position to the first position. As shown in FIGS. 2 and 3, the wire operation lever drive part 23 includes a guide shaft 24, a feed screw 25, a motor 26, and a button 27.

As shown in FIGS. 2 and 3, the guide shaft 24 passes through a guide hole provided in the wire operation lever 22 and extends in a direction connecting the first position and the second position of the wire operation lever 22. The wire operation lever 22 can move along the guide shaft 24 from the first position to the second position, or from the second position to the first position.

The feed screw 25 is a mechanism that converts rotational motion into linear motion. As shown in FIG. 2, a female screw formed on the wire operation lever 22 is engaged with the feed screw 25, and the feed screw 25 converts the rotational motion of the motor 26 into a linear motion of the wire operation lever 22.

The feed screw 25 extends in a direction connecting the first position and the second position of the wire operation lever 22, similarly to the guide shaft 24. The feed screw 25 moves the wire operation lever 22 from the first position to the second position, or from the second position to the first position.

The motor 26 is connected to the feed screw 25 and rotates the feed screw 25. A known DC motor or the like can be used as the motor 26. The motor 26 has sufficient torque to pull the wire operation part 62 that engages with the wire operation lever 22.

The button 27 is an operation button for operating the motor 26. When the button 27 is pressed, the motor 26 is operated so as to move the wire operation lever 22 from the first position to the second position.

The multi-lumen tube 200 is made of a flexible material such as silicone. As shown in FIGS. 4 and 5, the multi-lumen tube 200 is inserted through the internal space of the flexible tube part 3 and the bending piece 41.

In the multi-lumen tube 200, a first lumen 201 through which an observation means such as an endoscope 300 is inserted, and two second lumens 202 having an inner diameter smaller than that of the first lumen 201 and through which the treatment instrument 400 is inserted are provided over the entire length. The first lumen 201 and the second lumen 202 are both open at the proximal end side and the distal end side.

As shown in FIGS. 1, 4, and 5, the endoscope 300 is inserted into the first lumen 201 of the multi-lumen tube 200, and an imaging part 301 provided at the distal end of the insertion part of the endoscope 300 protrudes from the distal end of the overtube 1.

As shown in FIGS. 1, 4, and 5, the treatment tool 400 is inserted into the second lumen 202 of the multi-lumen tube 200, and a treatment part 401 such as a grip provided at the distal end of the insertion part of the treatment tool 400 protrudes from the distal end of the overtube 1.

The affected part is treated by the imaging part 301 of the endoscope 300 protruding from the distal end of the overtube 1 and the treatment part 401 of the treatment instrument 400.

As shown in FIG. 1, the treatment tool 400 is mounted on a mounting part 500 provided on the carriage D. The mounting part 500 can move the treatment tool 400 forward and backward relative to the carriage D in the longitudinal axis direction.

Next, the operation of the overtube device 100 will be described with reference to FIGS. 10 to 14. Here, the operation of inserting the overtube 1 into the large intestine L of the patient will be described.

First, the multi-lumen tube 200 is inserted through the overtube 1, and the endoscope 300 is inserted through the multi-lumen tube 200 of the overtube 1.

Figure 10:
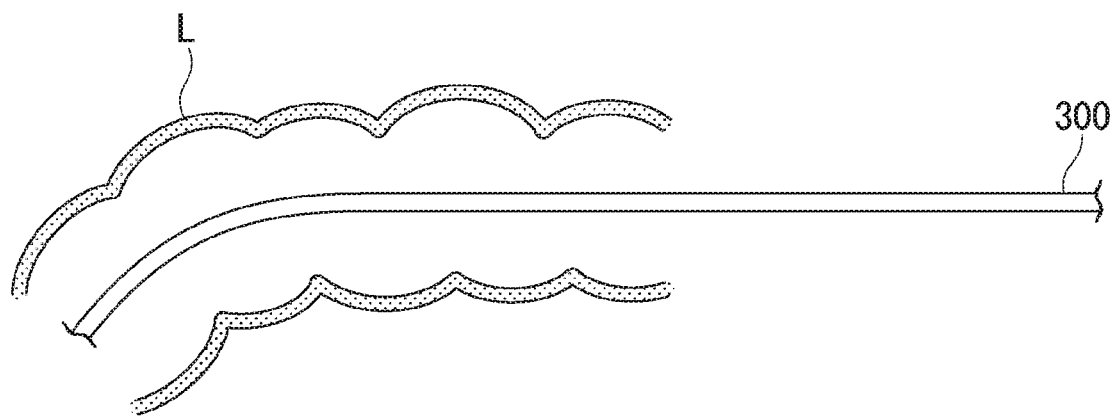
FIG. 10 is a diagram showing the operation of the overtube device.

Next, as shown in FIG. 10, an endoscope 300 having an active bending part at the distal end is inserted into the large intestine L of the patient. The operator inserts the distal end of the insertion part of the endoscope 300 to the treatment affected part of the large intestine L while actively bending the active bending part according to the curved shape of the large intestine L.

Figure 11:
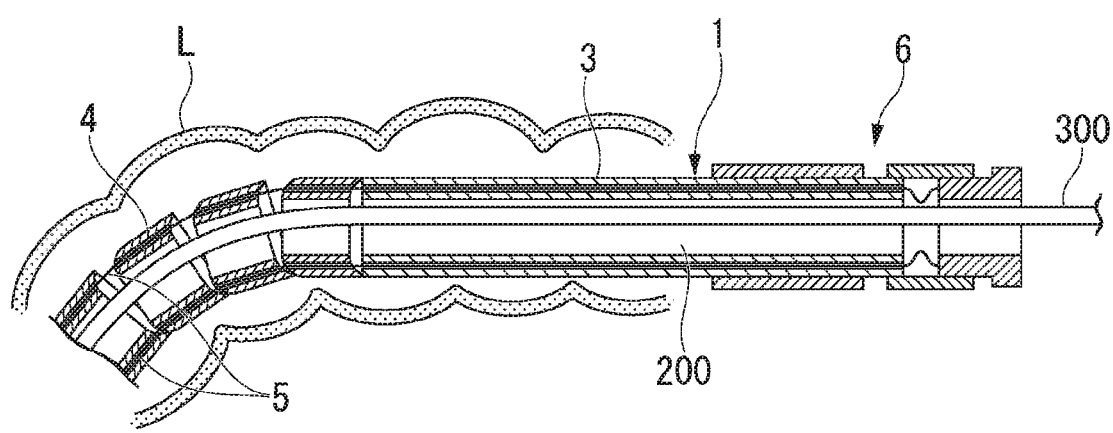
FIG. 11 is a diagram showing the operation of the overtube device.

Next, as shown in FIG. 11, the operator inserts the multi-lumen tube 200 and the overtube 1 along the endoscope 300. Since the wire 5 is loose, the shape lock function of the bending part 4 is invalidated, and the bending part 4 of the overtube 1 is inserted while being bent along the curved shape of the endoscope 300.

Figure 12:
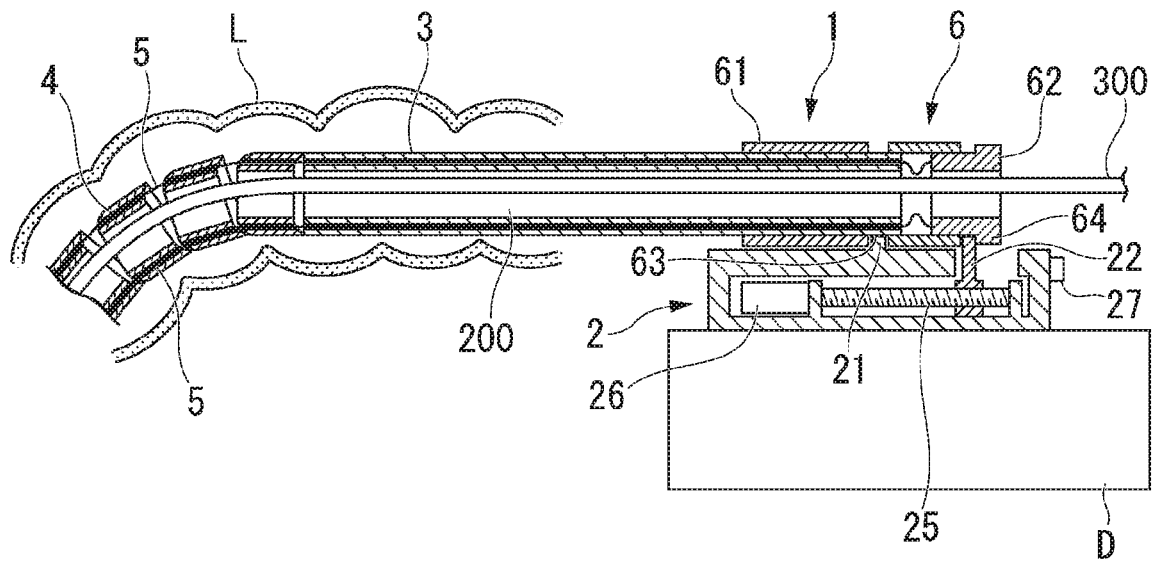
FIG. 12 is a diagram showing the operation of the overtube device.

Next, as shown in FIG. 12, the operator mounts (attaches) the operation part 6 on the overtube base 2. The wire operation lever 22 is provided at the first position, and the operator can engage the advance/retreat stopper 21 with the advance/retreat stopper engaging part 63 and engage the wire operation lever 22 with the wire operation lever engaging part 64.

The overtube 1 is fixed so as not to advance and retract in the longitudinal axis direction with respect to the patient being treated. In this state, the shape lock function of the bending part 4 is still invalidated.

Figure 13:
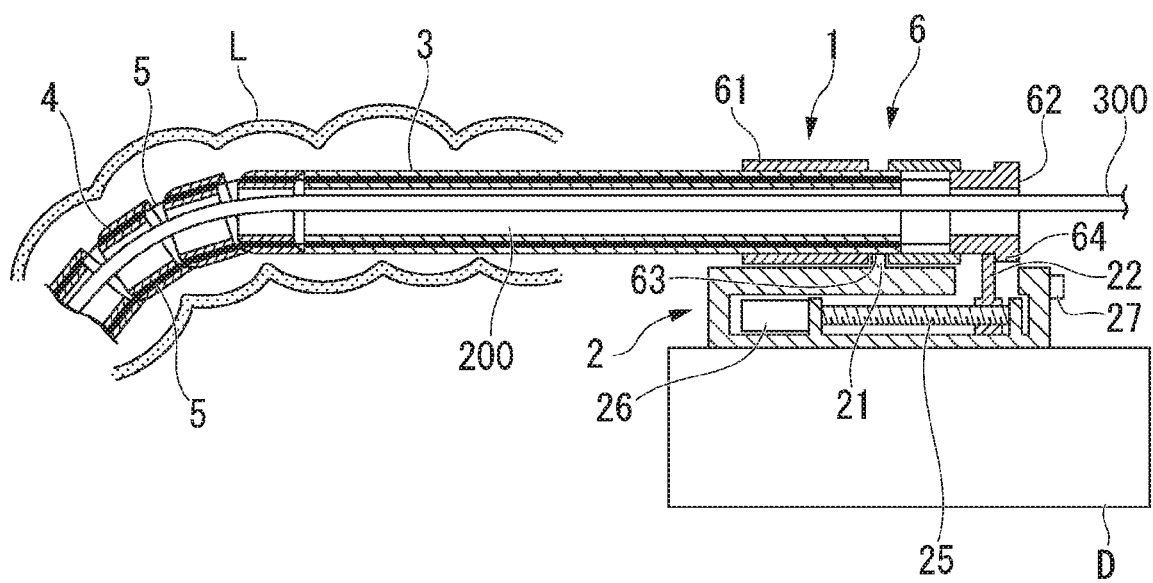
FIG. 13 is a diagram showing the operation of the overtube device.

Next, as shown in FIG. 13, the operator pushes the button 27 to move the wire operation lever 22 from the first position to the second position. The wire operation part 62 pulls the wire 5 toward the proximal end part of the wire 5 to hold the state where the wire 5 is pulled, and activates the shape lock function of the bending part 4. That is, the overtube base 2 can hold the wire 5 in a state where the wires 5 (the plurality of wires 5) are simultaneously pulled toward the proximal end until the curved shape of the bending part 4 is held.

Figure 14:
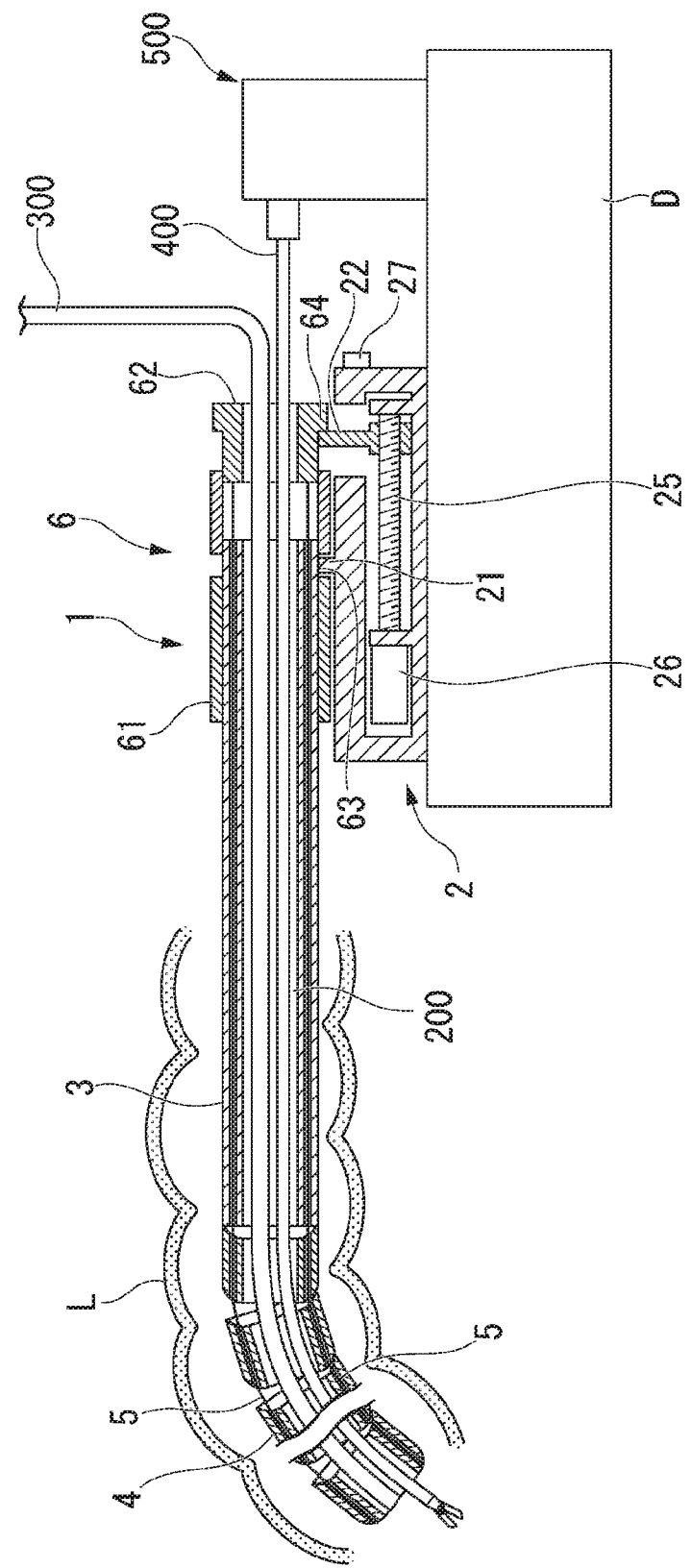
FIG. 14 is a diagram showing the operation of the overtube device.

Next, as shown in FIG. 14, the operator inserts the treatment instrument 400 into the second lumen 202 of the multi-lumen tube 200. The overtube 1 whose shape is temporarily fixed can more reliably guide the distal end of the treatment instrument 400 to the distal end of the overtube 1.

The proximal end of the treatment tool 400 is attached to the mounting part 500. The operator operates the mounting part 500 to advance and retract the treatment tool 400 relative to the carriage D in the longitudinal axis direction. The insertion part of the treatment tool 400 advances and retracts guided by the second lumen 202 of the multi-lumen tube 200.

The operator treats the affected part with the imaging part 301 of the endoscope 300 protruding from the distal end of the overtube 1 and the treatment part 401 of the treatment tool 400. The overtube 1 whose shape is temporarily fixed can stably arrange the endoscope 300 and the treatment tool 400 when treating the affected part of the large intestine L.

After the overtube 1 is fixed so as not to advance and retract in the longitudinal axis direction, the shape lock function is activated. That is, when the shape lock function is activated, the advance/retreat operation of the overtube 1 is fixed.

Therefore, the overtube device 100 can prevent a part of the overtube 1 whose shape is temporarily fixed from coming into contact with the inner wall of the large intestine L and reduce discomfort felt by the patient during treatment.

When the overtube 1 is advanced or retracted in order to change the treatment target diseased part or the like, the operator pulls up the operation part 6 from the overtube base 2 to separate them. By this operation, the engagement between the advance/retreat stopper 21 and the advance/retreat stopper engaging part 63 is released, and the engagement between the wire operation lever 22 and the wire operation lever engaging part 64 is also released. That is, when the overtube 1 is advanced or retracted, the shape lock function of the bending part 4 is automatically invalidated.

Therefore, the overtube device 100 can prevent a part of the overtube 1 whose shape is temporarily fixed from coming into contact with the inner wall of the large intestine L and reduce discomfort felt by the patient during treatment.

Effects of the First Embodiment

According to the overtube device 100 of the present embodiment, when the shape lock function is activated, the advance/retreat operation of the overtube 1 is fixed. Further, when the overtube 1 is advanced or retracted, the shape lock function of the bending part 4 is automatically invalidated. Therefore, the overtube device 100 can prevent a part of the overtube 1 whose shape is temporarily fixed from coming into contact with the inner wall of the large intestine L and reduce discomfort felt by the patient during treatment.

Further, according to the overtube device 100 of the present embodiment, the overtube 1 is mounted (attached) on the overtube base 2 whose relative position with the bed B where the patient under treatment lies is fixed, thereby the advance/retreat operation of the overtube 1 can be easily fixed. In addition, the shape lock function can be easily activated simply by operating the button 27.

Further, according to the overtube device 100 of the present embodiment, the overtube 1 can be immediately advanced and retracted by removing the operation tube 6 from the overtube base 2, and at the same time, the shape lock function of the bending part 4 is invalidated.

The operation burden on the operator during the treatment can be reduced, and the operator can concentrate on the treatment.

The first embodiment of the present invention has been described in detail with reference to the drawings. However, the specific configuration is not limited to this embodiment, and design changes and the like within the scope of the present invention are included. In addition, the constituent elements shown in the above-described first embodiment and modified examples shown below can be combined as appropriate.

Modified Example

For example, although the bending part 4 of the above embodiment does not have a function which bends actively, the aspect of the bending part 4 is not limited to this. For example, the overtube 1 may have an active bending part that is actively bent at least in a part of the bending part 4. When it has an active bending part, the overtube 1 may have an angle wire that bends the active bending part.

Further, although the multi-lumen tube 200 is inserted into the overtube 1 of the above embodiment, a plurality of thimble lumen tubes may be used instead of the multi-lumen tube 200.

Further, in the above embodiment, the advance/retreat stopper 21 is a convex member and the advance/retreat stopper engaging part 63 is a concave member. However, the modes of the advance/retreat stopper 21 and the advance/retreat stopper engaging part 63 are not limited to this. The advance/retreat stopper 21 and the advance/retreat stopper engaging part 63 may be any shape as long as they are engaged and the overtube base 2 can fix the overtube 1 so as not to advance or retreat in the longitudinal axis direction. For example, the advance/retreat stopper may be a concave member, and the advance/retreat stopper engaging part may be a convex member.

Moreover, the wire operation lever 22 of the above embodiment was a convex member, and the wire operation lever engaging part 64 was also a convex member. However, the mode of the wire operation lever 22 and the wire operation lever engaging part 64 is not limited to this. The wire operation lever 22 and the wire operation lever engaging part 64 may be any shape as long as they are engaged and the relative position between the wire operation part 62 and the operation part main body 61 can be kept constant. For example, the wire operation lever may be a concave member, and the wire operation lever engaging part may be a convex member.

The number of wires 5 and wire lumens (31, 42) may be other than four.

Figure 15:
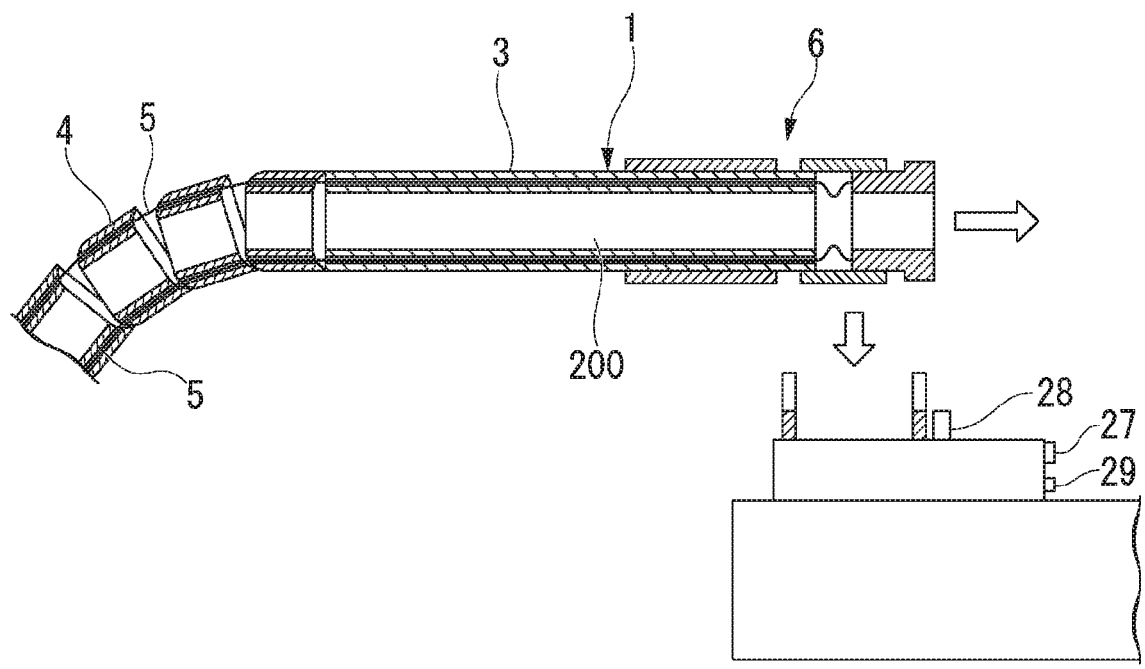
FIG. 15 is a side view of a modified example of the overtube device.
Figure 16:
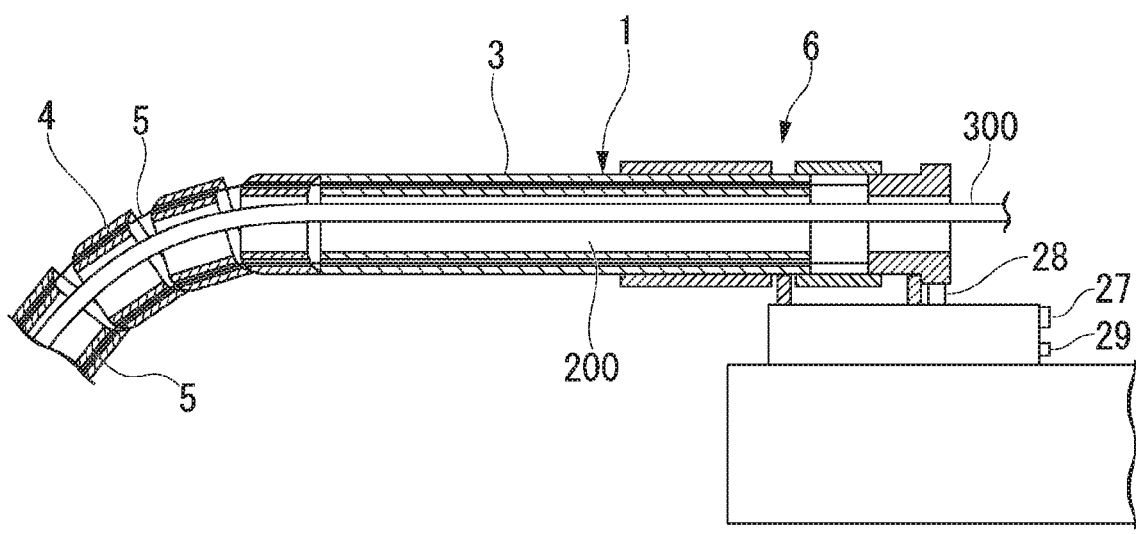
FIG. 16 is a side view of a modified example of the overtube device.

Further, the overtube base 2 may include an engagement sensor 28 as shown in FIGS. 15 and 16. The engagement sensor 28 is a contact sensor provided at or near the advance/retreat stopper 21, and detects that the advance/retreat stopper 21 and the advance/retreat stopper engaging part 63 are engaged and contacted. The detection result of the engagement sensor 28 is used to control the wire operation lever 22. For example, the operation of the button 27 may be made effective only when the engagement sensor 28 detects these engagements, and the overtube base 2 may be configured to move the wire operation lever 22 to the second position. By controlling in this way, it is possible to prevent the wire operation lever 22 from operating due to an erroneous operation of the button 27. Further, when the engagement sensor 28 detects the release of engagement, the overtube base 2 may be controlled to return the wire operation lever 22 to the first position.

Moreover, the overtube base 2 may have the engagement display part 29, as shown in FIGS. 15 and 16. The engagement display part 29 is a display device composed of LEDs or the like. When the engagement sensor 28 detects that the advance/retreat stopper 21 and the advance/retreat stopper engaging part 63 are in contact with each other, the engagement display part 29 performs a display which shows that, for example, LED lighting. The operator can easily grasp whether the advance/retreat stopper 21 and the advance/retreat stopper engaging part 63 are engaged by seeing the engagement display part 29.

Figure 17:
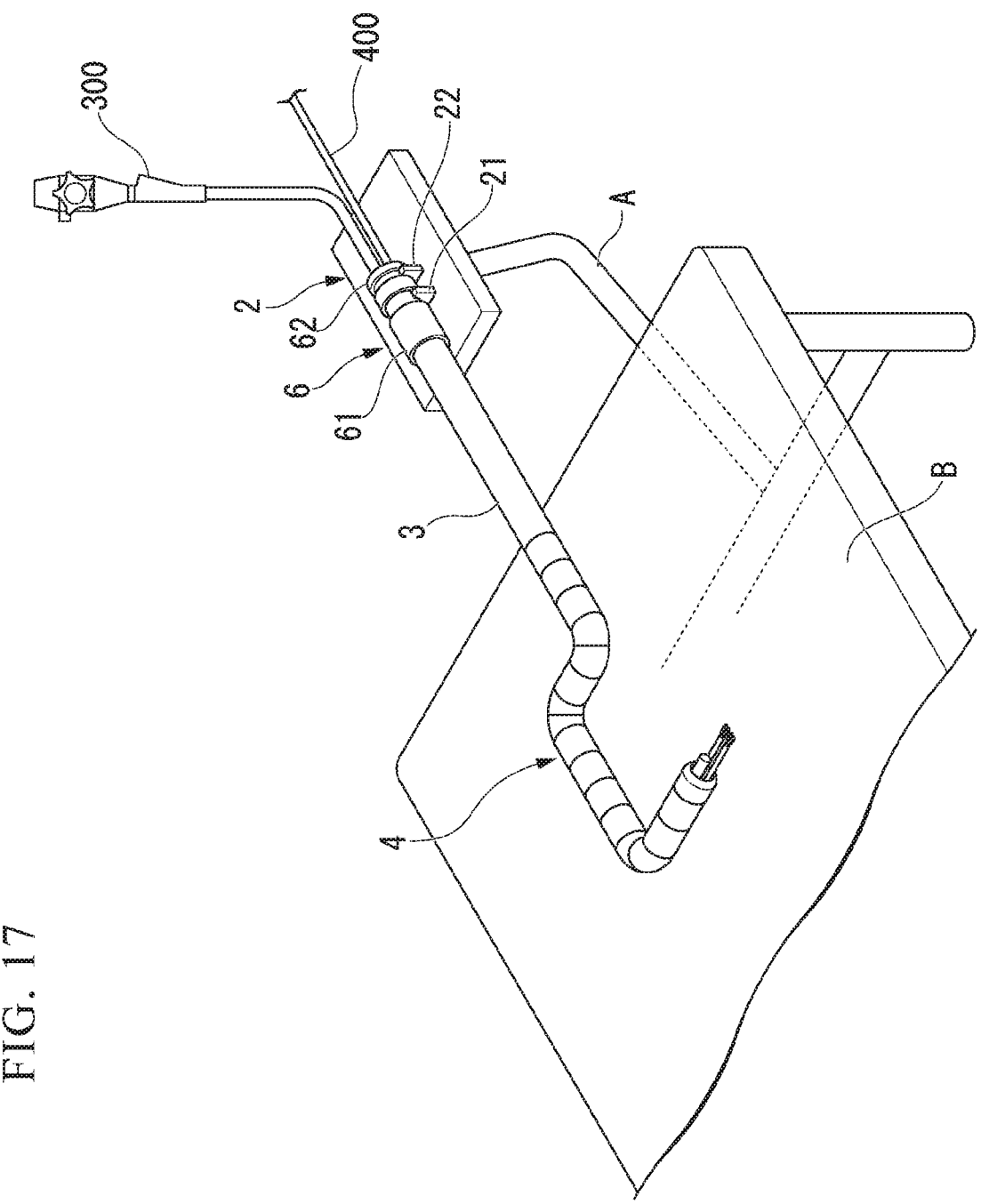
FIG. 17 is a diagram showing an overall configuration of a modified example of the overtube device.
Figure 18:
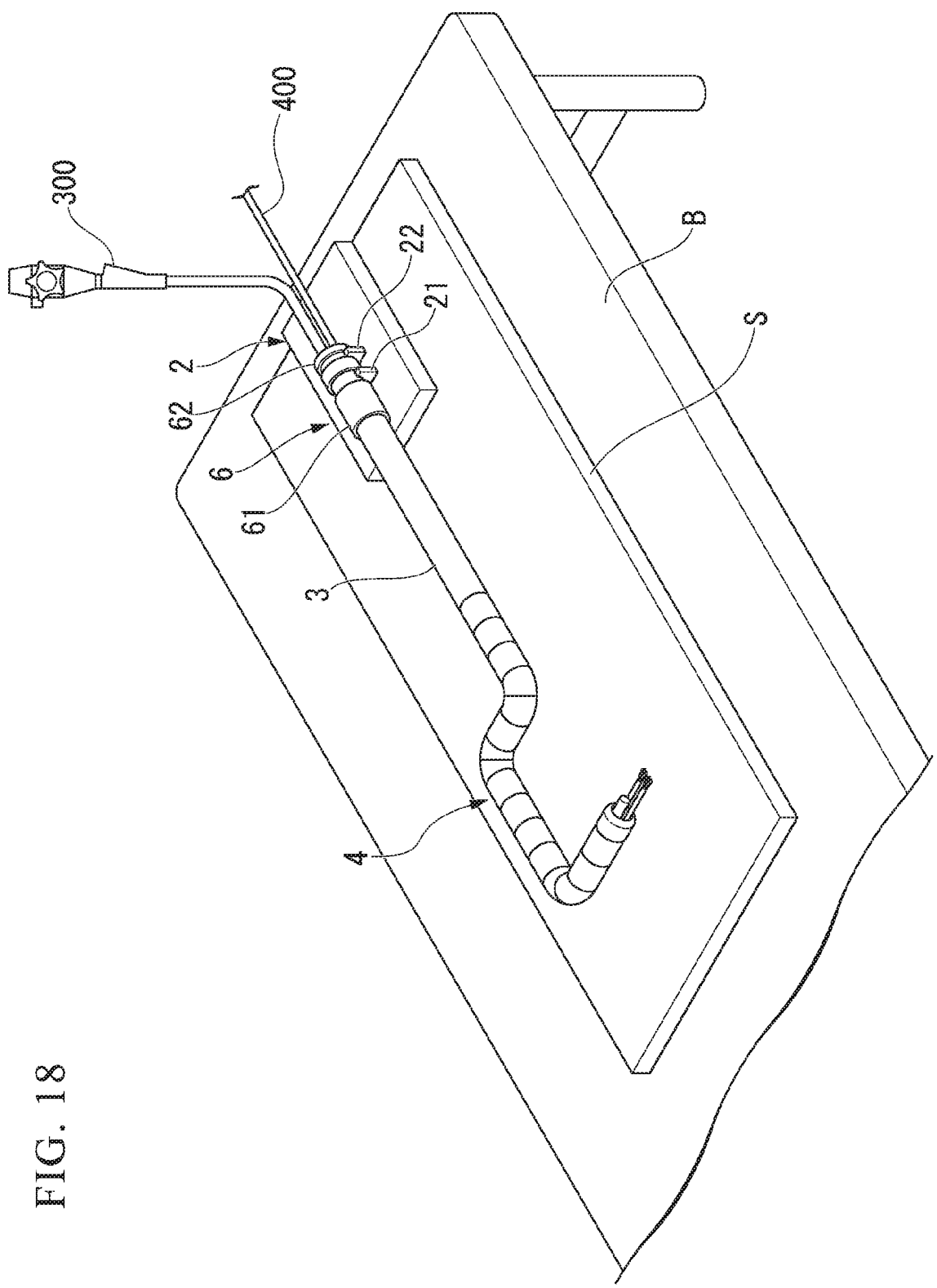
FIG. 18 is a diagram showing an overall configuration of a modified example of the overtube device.

Moreover, in the above embodiment, the overtube base 2 was fixed on the carriage D with casters. The fixing mode of the overtube base 2 is not limited to this. For example, as shown in FIG. 17, the overtube base 2 may be fixed to an arm A attached to a bed B where the patient lies. Further, as shown in FIG. 18, the overtube base 2 may be fixed to a seat S mounted (attached) on the bed B where the patient lies.

As long as the relative position between the position where the patient under treatment into which the overtube 1 is inserted lies and the overtube base 2 does not change during the treatment, the fixing manner of the both may be any.

Moreover, in the above embodiment, the second position of the wire operation lever 22 was preset. However, the aspect of the second position is not limited to this. For example, the tension or the pulling amount of the wire 5 is sensed, and the position of the wire operation lever 22 when the wire 5 is pulled until the tension or the pulling amount of the wire 5 exceeds a predetermined threshold may be set as the second position. By sensing the tension or the pulling amount of the wire 5, the second position can be flexibly set in consideration of the looseness of the wire 5, the elongation rate of the wire 5 itself, and the like in the initial state of the motor 26 or the feed screw 25.

The pulling amount of the wire 5 may be detected by appropriately adopting a known detection method. For example, the pulling amount may be detected by a position sensor using a photo interrupter, or may be controlled by an encoder or the like.

Second Embodiment

A second embodiment of the present invention will be described with reference to FIGS. 19 and 20. The present embodiment is different from the first embodiment in the manner of mounting (attaching) on the overtube and the overtube base. In the following description, components that are the same as those already described are assigned the same reference numerals and redundant description is omitted.

Figure 19:
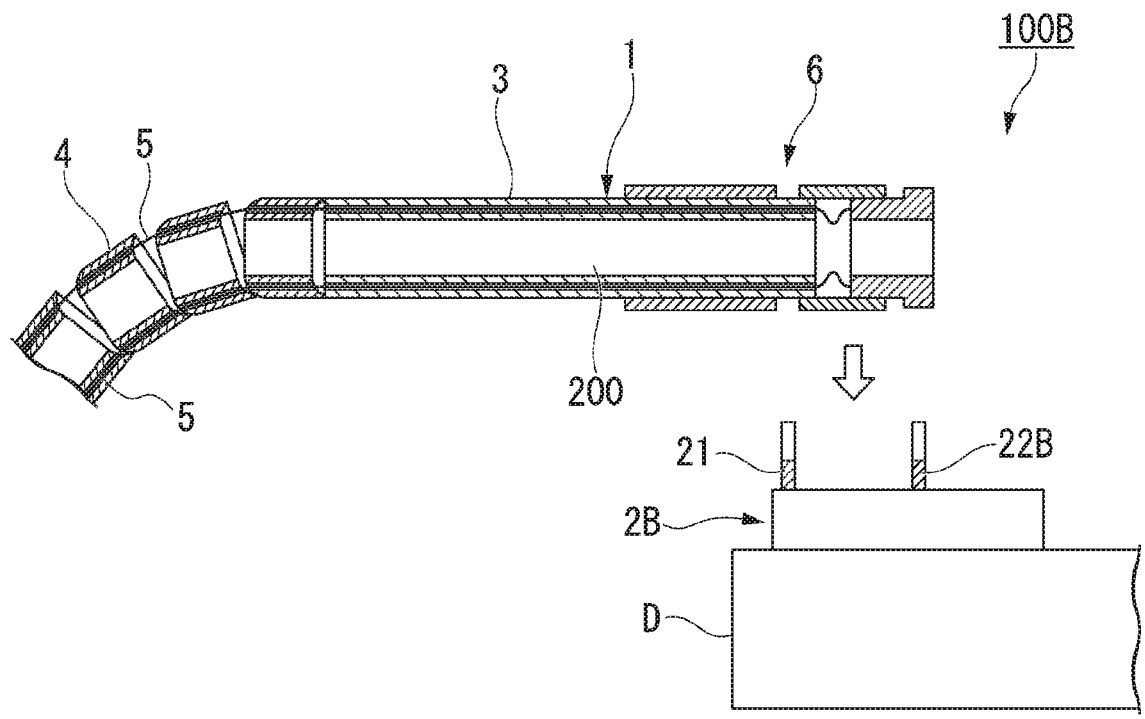
FIG. 19 is a cross-sectional view of an overtube device according to a second embodiment of the present invention.
Figure 20:
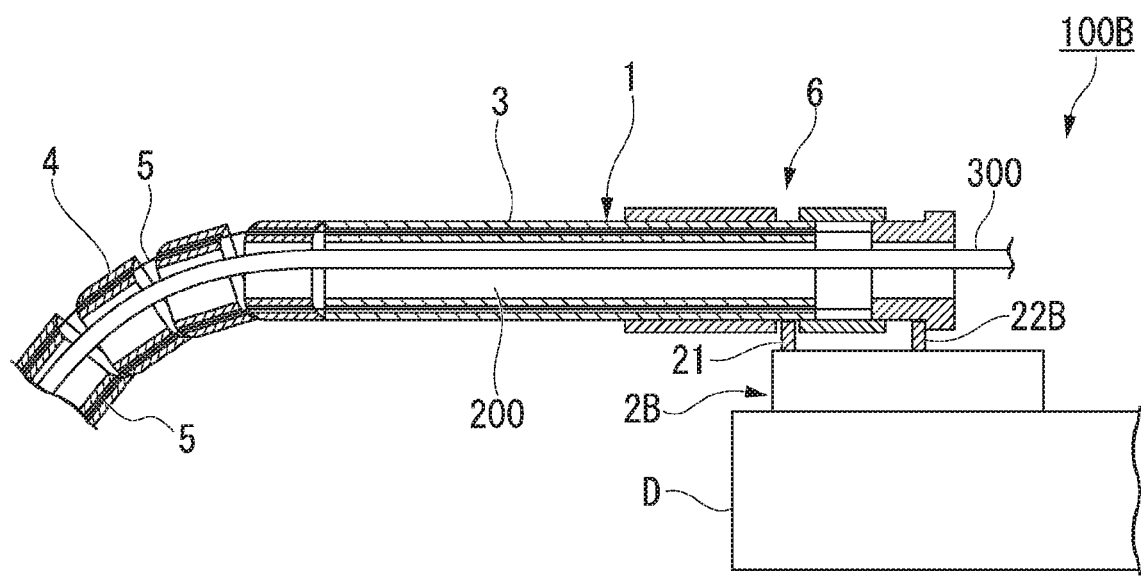
FIG. 20 is a sectional view of the overtube device.

FIGS. 19 and 20 are diagrams showing an overall configuration of an overtube device 100B according to the present embodiment.

The overtube device 100B includes an overtube 1 and an overtube base 2B.

FIG. 19 is an overall configuration diagram of the overtube device 100B before the overtube 1 is mounted (attached) to the overtube base 2B.

FIG. 20 is an overall configuration diagram of the overtube device 100B when the overtube 1 is mounted (attached) on the overtube base 2B.

As shown in FIGS. 19 and 20, the overtube base 2B includes an advance/retreat stopper 21 and a wire operation lever 22B. The overtube base 2B does not have a wire operation lever drive part, and the wire operation lever 22B is fixed in one position. The wire operation lever 22B is fixed at a position corresponding to the second position of the first embodiment.

The operation of the overtube device 100B will be described with reference to FIG. 19 and FIG. 20.

As shown in FIG. 19, before the operation part 6 is mounted (attached) to the overtube base 2B, the shape lock function of the bending part 4 is invalidated, and the bending part 4 of the overtube 1 is inserted while being bent along the curved shape of the endoscope 300.

When mounting (attaching) the operation part 6 to the overtube base 2B, the operator engages the advance/retreat stopper 21 with the advance/retreat stopper engaging part 63. At the same time, the operator engages the wire operation lever 22B with the wire operation lever engaging part 64 while pulling the wire operation part 62 toward the proximal end side. The wire operation part 62 holds the state where the wire 5 is pulled, and activates the shape lock function of the bending part 4. That is, the overtube base 2B can hold the state in which the wires 5 (the plurality of wires 5) are simultaneously pulled to the proximal end side until the curved shape of the bending part 4 is held.

At the same time that the overtube 1 is fixed so that it cannot advance and retract in the longitudinal axis direction, the shape lock function is activated.

At the same time that the overtube 1 is fixed so as not to advance and retract in the longitudinal axis direction, the shape lock function is activated. That is, when the shape lock function is activated, the advance/retreat operation of the overtube 1 is fixed.

Therefore, the overtube device 100B can prevent a part of the overtube 1 whose shape is temporarily fixed from coming into contact with the inner wall of the large intestine L, thereby reducing discomfort felt by the patient during treatment.

When the overtube 1 is advanced or retracted in order to change the affected part to be treated, the operator pulls up the operation part 6 from the overtube base 2B and separates both. By this operation, the engagement between the advance/retreat stopper 21 and the advance/retreat stopper engaging part 63 is released, and the engagement between the wire operation lever 22B and the wire operation lever engaging part 64 is also released. That is, when the overtube 1 is advanced or retracted, the shape lock function of the bending part 4 is automatically invalidated.

Therefore, the overtube device 100B can prevent a part of the overtube 1 whose shape is temporarily fixed from coming into contact with the inner wall of the large intestine L, thereby reducing discomfort felt by the patient during treatment.

Effect of the Second Embodiment

According to the overtube device 100B of the present embodiment, when the shape lock function is invalidated, the advance/retreat operation of the overtube 1 is fixed. Further, when the overtube 1 is advanced or retracted, the shape lock function of the bending part 4 is automatically invalidated. Therefore, the overtube device 100B can prevent a part of the overtube 1 whose shape is temporarily fixed from coming into contact with the inner wall of the large intestine L, thereby reducing discomfort felt by the patient during treatment.

Moreover, according to the overtube device 100B of the present embodiment, compared with the overtube device 100 of the first embodiment, it can be produced cheaply and easily.

Further, according to the overtube device 100B of the present embodiment, by removing the operation part 6 from the overtube base 2B, the overtube 1 can be immediately advanced or retracted, and at the same time, the shape lock function of the bending part 4 is invalidated.

The operation burden on the operator during the treatment can be reduced, and the operator can concentrate on the treatment.

What is claimed is:

1. An overtube device comprising:
    a tube body comprising a bending part and a main body part disposed proximally relative to the bending part;
    a wire having a distal end part fixed to the bending part, and a proximal end part, the wire extending along a longitudinal axis of the main body part;
    an operation part mounted on a proximal end side of the main body part, attached to the proximal end part of the wire, and configured to pull the wire to keep a curved shape of the bending part; and
    an overtube base configured to fix the tube body in a longitudinal axis direction so as not to advance and retract, and to hold the wire pulled toward the proximal end side of the main body part,
    wherein the overtube base is configured to be switchable between a first state and a second state,
    wherein in the first state, the operation part is separated from the overtube base, and the operation part does not pull the wire, and
    wherein in the second state, the operation part is attached to the overtube base, and the operation part pulls the wire.

2. The overtube device according to claim 1,
    wherein the operation part comprises:
        an operation part main body configured to be connected to the main body part; and
        a wire operation part that is held so as to be relatively movable with respect to the operation part main body and to which the proximal end part of the wire is attached, and
    wherein, by moving the wire operation part away from the operation part main body, the proximal end part of the wire is pulled away from the operation part main body.

3. The overtube device according to claim 2,
    wherein the operation part main body comprises an advance/retreat stopper engaging part,
    wherein the wire operation part comprises a wire operation lever engaging part,
    wherein the overtube base comprises:
        an advance/retreat stopper configured to engage with the advance/retreat stopper engaging part; and
        a wire operation lever configured to engage with the wire operation lever engaging part while keeping a relative position of the advance/retreat stopper constant, and
    wherein the operation part is configured to be mounted on the overtube base, so that the advance/retreat stopper is engaged with the advance/retreat stopper engaging part, and simultaneously the wire operation lever is engaged with the wire operation lever engaging part.

4. The overtube device according to claim 3,
    wherein the wire operation lever is configured to be movable to either a first position or a second position,
    wherein, when the wire operating lever is moved to the first position, the operation part does not pull the proximal end part of the wire away from the operation part main body, and a holding of the curved shape is released, and
    wherein, when the wire operating lever is moved to the second position, the operation part pulls the proximal end part of the wire away from the operation part main body, and the curved shape is held.

5. The overtube device according to claim 4,
    wherein the overtube base comprises a wire operation lever drive part configured to move the wire operation lever from the first position to the second position.

6. The overtube device according to claim 5,
    wherein the wire operation lever drive part is configured to receive a user input and to move the wire operation lever from the first position to the second position.

7. The overtube device according to claim 3,
    wherein an outer diameter of the advance/retreat stopper engaging part is smaller than an outer diameter of an other portion of the operation part main body, and
    wherein an outer diameter of the wire operation lever engaging part is larger than an outer diameter of an other portion of the wire operation part.

8. The overtube device according to claim 2,
    wherein the operation part main body comprises an advance/retreat stopper engaging part,
    wherein the wire operation part comprises a wire operation lever engaging part, and
    wherein the overtube base comprises:
        an advance/retreat stopper configured to engage with the advance/retreat stopper engaging part; and
        a wire operation lever configured to engage with the wire operation lever engaging part while keeping a relative position of the advance/retreat stopper constant.

9. The overtube device according to claim 8,
    wherein the wire operation lever is configured to, simultaneously with the advance/retreat stopper engaging with the advance/retreat stopper engaging part, engage with the wire operation lever engaging part when the operation part is mounted on the overtube base.

10. The overtube device according to claim 1,
    wherein the overtube base comprises an engagement sensor configured to detect that the operation part is mounted on the overtube base.

11. The overtube device according to claim 10,
    wherein the overtube base comprises an engagement display part, and
    wherein, when the engagement sensor detects a mounting of the operation part on the overtube base, the engagement display part is configured to display an indication of the mounting.

12. The overtube device according to claim 1,
    wherein the wire is a plurality of wires,
    wherein the operation part is attached to proximal end parts of the plurality of wires, and configured to pull the plurality of wires to keep a curved shape of the bending part, and
    wherein the overtube base is configured to simultaneously hold the plurality of wires pulled toward the proximal end side of the main body part.

13. The overtube device according to claim 1,
    wherein the overtube base is configured to be attached to a part of a circumference of the operation part.

14. The overtube device according to claim 1,
wherein the operation part comprises:
  an advance/retreat stopper engaging part; and
  a wire operation lever engaging part, and
wherein the overtube base comprises:
  an advance/retreat stopper configured to engage with the advance/retreat stopper engaging part; and
  a wire operation lever configured to engage with the wire operation lever engaging part while keeping a relative position of the advance/retreat stopper constant.

15. The overtube device according to claim 14,
wherein the wire operation lever is configured to, simultaneously with the advance/retreat stopper engaging with the advance/retreat stopper engaging part, engage with the wire operation lever engaging part when the operation part is mounted on the overtube base.

16. A method comprising:
a first inserting step of inserting an endoscope into a lumen around an affected area of a patient;
a second inserting step of inserting an overtube device into the lumen, the overtube device comprising:
  a tube body comprising a bending part and a main body part disposed proximally relative to the bending part;
  a wire having a distal end part fixed to the bending part, and a proximal end part, the wire extending along a longitudinal axis of the main body part;
  an operation part mounted on a proximal end side of the main body part, attached to the proximal end part of the wire, and configured to pull the wire to keep a curved shape of the bending part; and
  an overtube base configured to fix the tube body in a longitudinal axis direction so as not to advance and retract, and to hold the wire pulled toward the proximal end side of the main body part, wherein the overtube base is configured to be switchable between a first state and a second state, wherein in the first state, the operation part is separated from the overtube base, and the operation part does not pull the wire, and wherein in the second state, the operation part is attached to the overtube base, and the operation part pulls the wire,
  wherein the second inserting step comprises, while the overtube base is switched to be in the first state where the operation part is separated from the overtube base, controlling the operation part to not pull the wire while inserting the overtube device into the lumen guided by the endoscope;
a fixing step of switching the overtube base to be in the second state where the operation part is attached to the overtube base so that the tube body is fixed in the longitudinal axis direction and controlling the operation part to pull the wire to keep the curved shape of the bending part of the tube body; and
a third inserting step of inserting a treatment tool into the overtube.

17. The method according to claim 16, wherein, in the fixing step, switching the overtube base to be in the second state and controlling the operation part to pull the wire are performed at the same time.

* * * * *